United States Patent [19]

Brown et al.

[11] 4,316,904

[45] Feb. 23, 1982

[54] INDOLOPYRONE TETRAZOLES AND CARBOXAMIDOTETRAZOLES HAVING ANTIALLERGIC ACTIVITY

[76] Inventors: Richard E. Brown, 16 Ridge Dr., East Hanover, N.J. 07936; Paul C. Unangst, 3659 Middleton Dr., Ann Arbor, Mich. 48105

[21] Appl. No.: 78,632

[22] Filed: Sep. 25, 1979

Related U.S. Application Data

[63] Continuation-in-part of Ser. No. 912,645, Jun. 5, 1978, abandoned.

[51] Int. Cl.³ .................... A61K 31/41; C07D 257/02
[52] U.S. Cl. ................................ 424/269; 548/251; 548/254
[58] Field of Search ................ 548/251, 254; 424/269

[56] References Cited

U.S. PATENT DOCUMENTS 3,887,574  6/1975  Ellis et al. ........................... 548/251
4,028,383  6/1977  Brown et al. .................. 260/326.29

FOREIGN PATENT DOCUMENTS 2721021  11/1977  Fed. Rep. of Germany ...... 548/251

*Primary Examiner*—Donald G. Daus
*Assistant Examiner*—D. B. Springer
*Attorney, Agent, or Firm*—Stephen I. Miller

[57] ABSTRACT

Certain novel indolopyrone tetrazoles, carboxamidotetrazoles and their pharmaceutically acceptable salts are disclosed. These compounds are useful as antiallergic agents in mammals.

16 Claims, No Drawings

INDOLOPYRONE TETRAZOLES AND CARBOXAMIDOTETRAZOLES HAVING ANTIALLERGIC ACTIVITY

CROSS REFERENCE TO RELATED APPLICATION

This is a continuation-in-part of application Ser. No. 912,645 filed June 5, 1978, now abandoned.

BACKGROUND OF THE INVENTION

U.S. Pat. No. 4,028,383 describes a class of indolopyrone carboxylic acids and their esters which are useful antiallergic compounds. U.S. Pat. No. 4,110,464 claims a method for preventing allergic and asthmatic reactions in mammals upon administration of a compound chosen from among certain indolopyrone carboxylic acids and their esters.

The present invention describes a class of indolopyrone tetrazoles and carboxamidotetrazoles which possess enhanced activity when compared to the corresponding acids, for the prevention of allergic and asthmatic reactions in mammals.

SUMMARY OF THE INVENTION

The present invention relates to a compound of the formula I:

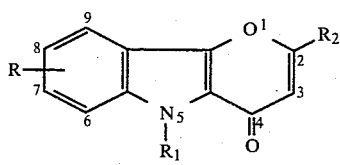

wherein

R is hydrogen, hydroxy, alkyl of from 1 to 6 carbon atoms, alkoxy of from 1 to 6 carbon atoms, halogen, trifluoromethyl, nitro, 6,8-dinitro, or 7,8-methylenedioxy; $R_1$ is hydrogen, alkyl of from 1 to 6 carbon atoms or phenyl;

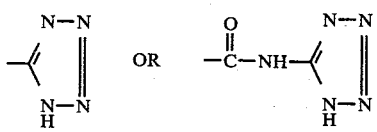

and the pharmaceutically acceptable salts thereof. Provided that when R is hydrogen and $R_1$ is phenyl; $R_2$ is not

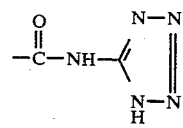

The preferred compounds of the invention are those wherein R is 6,8-dinitro, 7,8-methylenedioxy or is located in the 8-position; and the pharmaceutically acceptable salts thereof. Provided that when R is hydrogen and $R_1$ is phenyl; $R_2$ is not

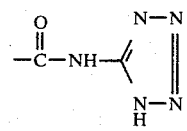

The most preferred compounds of the invention are those wherein R is 8-chloro, 8-methyl, 8-nitro or 6,8-dinitro; and the pharmaceutically acceptable salts thereof.

The invention also relates to a pharmaceutical composition comprising an antiallergic effective amount of a compound of formula I and the pharmaceutically acceptable salts thereof.

The invention also relates to a method of preventing the allergic response in a mammal which comprises administering to said mammal an antiallergic effective amount of a compound of formula I and the pharmaceutically acceptable salts thereof.

DESCRIPTION OF THE PREFERRED EMBODIMENTS

The compounds of the invention wherein $R_2$ is

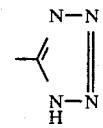

may be prepared from the corresponding acids or esters (described in U.S. Pat. No. 4,028,383) by methods familiar to those skilled in the art. For example, the properly substituted carboxylic acid may be converted to the corresponding acid halide such as the chloride by treatment with thionyl chloride or oxalyl chloride and converted to the acid amide by treatment with ammonia. The amide is dehydrated by treatment with, for example, p-toluenesulfonyl chloride and pyridine in dimethylformamide thereby producing the corresponding nitrile which when treated with sodium azide and aluminum chloride, for example, will yield the corresponding tetrazole. The above-described amides may also be prepared directly from the corresponding esters by treatment with, for example, gaseous ammonia by methods familiar to those skilled in the art. Other methods and reagents for converting carboxylic acids or esters into the corresponding tetrazoles will be familiar to those skilled in the art.

The compounds of the invention wherein $R_2$ is

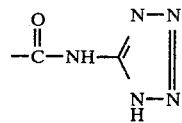

may be prepared from the corresponding acid halide, such as the above-described acid chloride, by treatment with 5-aminotetrazole. Alternatively, the properly substituted carboxylic acid may be directly coupled with 5-aminotetrazole; by use of such agents as N-ethoxycarbonyl-2-ethoxy-1,2-dihydroquinoline (EEDQ), dicyclohexylcarbodiimide (DCC) and the like.

Other compounds of the invention and intermediates thereto may be prepared by methods known to those skilled in the art. For example, an indolopyrone-2-carboxylic acid, unsubstituted in the carbocylic aromatic ring, may be either mono or di-nitrated by familiar methods.

The compounds of the invention are acidic in nature and form pharmaceutically acceptable salts with both organic and inorganic bases such as dimethylaminoethanol, the alkali metal and alkaline earth hydroxides and the alkali metal carbonates and bicarbonates such as lithium, sodium, potassium and calcium hydroxide, and the carbonates and bicarbonates of lithium, sodium and potassium. The salts are prepared by reacting the tetrazole or the carboxamidotetrazole with the desired base in the conventional manner. The tetrazoles, and the carboxamidotetrazoles differ from their respective salts somewhat in certain physical properties such as solubility in polar solvents, but the salts are otherwise equivalent to their respective acids for purposes of the invention.

The compounds of the invention can exist in unsolvated as well as solvated forms, including hydrated forms. In general, the solvated forms, with pharmaceutically-acceptable solvents such as water, ethanol and the like are equivalent to the unsolvated forms for purposes of the invention.

The alkoxy groups and alkyl groups contemplated by the invention comprise both straight and branched carbon chains of from 1 to 6 carbon atoms. Representative of such groups are methyl, ethyl, isopropyl, pentyl, 3-methylpentyl, methoxy, ethoxy, propoxy, 1-ethylbutoxy, pentoxy and the like.

The compounds of the invention are new chemical substances of value as pharmacological agents which prevent the allergic response in mammals by inhibition of the release of such allergic mediators, as histamine. The assay by which this utility was established is carried out as follows.

Rat Reaginic Passive Cutaneous Anaphylaxis (PCA)

The PCA test (D. J. Herzig, P. R. Schumann, E. J. Kusner, L. Robichaud, R. E. Giles, B. Dubnick, M. von Strandtmann, S. Klutchko, M. Cohen, and J. Shavel, Jr., "Immunopharmacology", M. E. Rosenthale and H. C. Mansmann, Eds., Spectrum Publications, Inc., New York, N.Y., 1975, pp. 103–124) involved immunization of rats with 1 mg of ovalbumin intramuscularly and approximately $10^{10}$ B. pertussis organisms as pertussis vaccine, intraperitoneally. Fourteen days later, the rats were bled and the serum was prepared. Suitable dilutions of antiserum were injected intradermally at various sites on the back of rats 48 h before an intravenous injection of 1 mg of ovalbumin in 1 ml of physiological saline and 0.25% Evans Blue. Thirty minutes later the animals were killed in ether, the dorsal skin was reflected, and the mean orthogonal diameter of the wheal was measured. For oral or intraperitoneal dosing, the drugs were suspended in 1% gum tragacanth in physiological saline and given 10–15 min before intravenous antigen challenge. For intravenous dosing, the compounds were dissolved in the saline/ovalbumin/Evans Blue solution and given with the antigen. If necessary, the compounds were first dissolved in a slight molar excess of sodium bicarbonate and then diluted into the antigen solution. Groups of five animals were used for all dose levels and control groups.

To quantitate the PCA test, the mean diameter of each wheal spot was graphed as a function of the relative antiserum concentration. The line, fitted by the least-squares equation, was extrapolated to the value at "zero" antiserum concentration (base value). The following equation was then used to calculate the percent inhibition:

$$\% \text{ inhibition} = \left[1 - \left(\frac{\text{diameter of drug-base value}}{\text{diameter of control-base value}}\right)\right] \times 100$$

The statistical significance of the results was determined by Student's t test ($p \leq 0.05$). An inhibition of 15% was significant. The test results obtained for the compounds of the invention as well as for the corresponding acids (U.S. Pat. No. 4,028,383) are given as percent inhibition in the following table.

TEST RESULTS

| R/R₁ | R₂* | Dose in mg/kg, i.p. | |
|---|---|---|---|
| | | 5 | 1 |
| H/CH₃ | T (a) | 100 | 87 |
| | C | 100 | 28 |
| | A | 100 | 30 |
| H/C₂H₅ | T (b) | 100 | 100 |
| | C | 100 | 12 |
| | A | — | 0 |
| H/φ | T (c) | 100 | 61 |
| | C | Inac. | — |
| | A | — | 13 |
| 8-Cl/CH₃ | T (d) | 100 | 46 |
| | C | 100 | 38 |
| | A | 23 | — |
| 8-CH₃/CH₃ | T (e) | 100 | 25 |
| | C | 100 | 33 |
| | A | — | 18 |
| 8-NO₂/CH₃ | C | 100 | 42 |
| | A | 100 | 1 |
| 6,8-di-NO₂/CH₃ | C | 48 | — |
| | A | 0 | — |

*T = tetrazole
C = carboxamidotetrazole
A = carboxylic acid
(a) This compound displayed 39% and 12% inhibition when administered, orally at doses of 5 and 2 mg/kg respectively.
(b) This compound displayed 70% inhibition when administered, orally at 5 mg/kg.
(c) This compound displayed 32% inhibition when administered, orally at 2 mg/kg and 28% inhibition when administered, intraveneously at 0.1 mg/kg.
(d) This compound displayed 33% inhibition when administered, orally at 5 mg/kg.
(e) This compound displayed 56% inhibition when administered, orally at 5 mg/kg.

The compositions of the invention can be administered in a variety of dosage forms such as tablets or capsules and liquids for oral or parenteral use. The dosage forms may contain, in addition to the active component, any of the usual compounding excipients such as flavors, colors, stabilizers and tableting materials such as binders, fillers, lubricants and the like. The dosage requirements may vary with the particular composition being employed and may depend on the severity of the symptoms being presented and the size of the mammal being treated. In general, an amount of from about 0.1 to about 10 mg/kg of the active component in single or divided doses will be sufficient to accomplish the method of the invention.

The invention is illustrated by the following examples.

EXAMPLE 1

5-Methyl-2(1H-tetrazol-5-yl)pyrano[3,2-b]indol-4(5H)-one

To a mixture of 4.0 g (17.9 mmole) 4,5-dihydro-5-methyl-4-oxopyrano[3,2-b]indole-2-carbonitrile and 4.0 g (61.6 mmole) sodium azide in 500 ml THF under nitrogen, was added 5.3 g (39.8 mmole) anhydrous aluminum chloride in portions over 20–30 min. The mixture was stirred at reflux for 21 hr, cooled, and an additional 2.0 g (30.8 mmole) sodium azide and 4.8 g (36.3 mmole) aluminum chloride were similarly added. Stirring at reflux was continued for a total of 61 hr. The reaction mixture was cooled in ice and then added cautiously to 2.0 L ice/water. Acidification with 4 N HCl ($HN_3$ evolved) at $\leq 5°$ C. yielded a tan solid which was filtered, digested on the steam bath for 30 min. with 200 ml water, and then refiltered warm. The crude product was stirred in 150 ml acetone for 20 min., then the solid was again recovered by filtering. Recrystallization from aqueous DMF yielded yellow plates of mp 270° C. dec.

EXAMPLE 2

5-Phenyl-2(1H-tetrazol-5-yl)pyrano[3,2-b]indol-4(5H)-one

In a manner analogous to that of Example 1, the title compound was prepared from 4,5-dihydro-4-oxo-5-phenylpyrano[3,2-b]indole-2-carbonitrile. Reflux time was 87 hr, and the acetone treatment before recrystallization was omitted. Two recrystallizations from aqueous DMF yielded tan needles of mp 245° C. dec.

EXAMPLE 3

5,8-Dimethyl-2-(1H-tetrazol-5-yl)pyrano[3,2-b]indol-4(5H)-one

In a manner analogous to that of Example 1, the title compound was prepared from 4,5-dihydro-5,8-dimethyl-4-oxopyrano[3,2-b]indole-2-carbonitrile. Two recrystallizations from aqueous DMF yielded yellow solid of mp 257° C. dec.

EXAMPLE 4

5-Ethyl-2-(1H-tetrazol-5-yl)pyrano[3,2-b]indol-4(5H)-one

In a manner analogous to that of Example 1, the title compound was prepared from 5-ethyl-4,5-dihydro-4-oxopyrano[3,2-b]indole-2-carbonitrile. Two recrystallizations from aqueous DMF yielded yellow powder of mp 255° C. dec.

EXAMPLE 5

8-Chloro-5-methyl-2-(1H-tetrazol-5-yl)pyrano[3,2-b]indol-4(5H)-one

In a manner analogous to that of Example 1, the title compound was prepared from 8-chloro-4,5-dihydro-5-methyl-4-oxopyrano[3,2-b]indole-2-carbonitrile. Several recrystallizations from aqueous DMF yielded yellow solid of mp 265° C. dec.

EXAMPLE 6

8-Chloro-4,5-dihydro-5-methyl-4-oxo-N-1H-tetrazol-5-ylpyrano[3,2-b]indole-2-carboxamide A mixture of 2.5 g (9.1 mmole) 8-chloro-4, 5-dihydro-5-methyl-4-oxopyrano[3,2-b]indole-2-carboxylic acid and 4.8 g (19.7 mmole) N-ethoxycarbonyl-2-ethoxy-1,2-dihydroquinoline (EEDQ) in 300 ml benzene was stirred for 45 min under nitrogen. To the reaction mixture was added 1.1 g (10.7 mmole) of 5-aminotetrazole monohydrate, and stirring was continued for a total of 88 hrs. The precipitate that had formed was filtered, stirred overnight in 50 ml of methanol, and refiltered. Two recrystallizations from DMF yielded a yellow solid of mp 300° C. dec.

EXAMPLE 7

4,5-Dihydro-5-methyl-4-oxo-N-1H-tetrazol-5-ylpyrano[3,2-b]indole-2-carboxamide In a manner analogous to that of Example 6, the title compound was prepared from 4,5-dihydro-5-methyl-4-oxopyrano[3,2-b]indole-2-carboxylic acid. Several recrystallizations from DMF yielded a yellow solid of mp 295° C. dec.

EXAMPLE 8

5-Ethyl-4,5-dihydro-4-oxo-N-1H-tetrazol-5-ylpyrano[3,2-b]indole-2-carboxamide In a manner analogous to that of Example 6, the title compound was prepared from 5-ethyl-4,5-dihydro-4-oxopyrano[3,2-b]indole-2-carboxylic acid. Several recrystallizations from DMF yielded yellow crystals of mp 288° C. dec.

EXAMPLE 9

4,5-Dihydro-5,8-dimethyl-4-oxo-N-1H-tetrazol-5-ylpyrano[3,2-b]indole-2-carboxamide In a manner analogous to that of Example 6, the title compound was prepared from 4,5-dihydro-5,8-dimethyl-4-oxopyrano[3,2-b]indole-2-carboxylic acid. Several recrystallizations from DMF yielded yellow crystals of mp 290° C. dec.

EXAMPLE 10

4,5-Dihydro-5-methyl-8-nitro-4-oxo-N-1H-tetrazol-5-ylpyrano[3,2-b]indole-2-carboxamide A mixture of 4.7 g (16.4 mmole) 4,5-dihydro-5-methyl-8-nitro-4-oxopyrano[3,2-b]indole-2-carboxylic acid and 3.8 g (23.4 mmole) 1,1′carbonyl-diimidazole in 100 ml DMF was heated at 60° C. for one hour and then cooled to room temperature. In a separate flask, a mixture of 1.8 g (17.5 mmole) 5-aminotetrazole monohydrate and 5.4 g (53.1 mmole) triethylamine were combined in 50 ml DMF. This mixture was cooled in an ice bath while 5.8 g (52.8 mmole) chlorotrimethylsilane was added in one portion. Stirring in ice was continued for one hour, followed by an additional two hours with the ice bath removed. The triethylamine mixture was then added to the original carboxylic acid mixture, and the new mixture was heated on a steam bath for one hour. The mixture was cooled, and the precipitated triethylamine hydrochloride was filtered and discarded. The filtrate was added to 500 g ice/water, the mixture was filtered by gravity, and the filtrate was acidified with 4 N hydrochloric acid. The precipitated crude product was filtered, washed with water and recrystallized twice from DMF-water to yield yellow solid of mp 295° C. dec.

EXAMPLE 11

4,5-Dihydro-5-methyl-6,8-dinitro-4-oxo-N-1H-tetrazol-5-ylpyrano[3,2-b]indole-2-carboxamide In a manner analogous to that of Example 10, the title compound was prepared from 4,5-dihydro-5-methyl-6,8-dinitro-4-oxo-pyrano[3,2-b]indole-2-carboxylic acid. Two recrystallizations from DMF-water yielded tan solid of mp 294° C. dec.

INTERMEDIATES

Preparation 1

4,5-Dihydro-5-methyl-4-oxopyrano[3,2-b]indole-2-carboxamide

A suspension of 11.0 g (40.7 mmole) of ethyl 4,5-dihydro-5-methyl-4-oxopyrano[3,2-b]indole-2-carboxylate in 500 ml ethanol was stirred in ice while gaseous ammonia was added until the reaction mixture temperature reached 20° C. (ca. 10 min). The ice bath was removed, and stirring at room temperature was continued for a total of 24 hr. The light yellow solid was filtered and washed with a little cold ethanol. Recrystallization from 50% aqueous DMF gave light yellow needles of mp >295° C.

Preparation 2

4,5-Dihydro-5-ethyl-4-oxopyrano[3,2-b]indole-2-carboxamide

In a manner analogous to that of Preparation 1, the title compound was prepared from ethyl 4,5-dihydro-5-ethyl-4-oxopyrano[3,2-b]indole-2-carboxylate. Several recrystallizations of the final product from aqueous DMF yielded tan needles of mp 224°–226° C.

Preparation 3

4,5-Dihydro-4-oxo-5-phenylpyrano[3,2-b]indole-2-carboxamide

In a manner analogous to that of Preparation 1, the title compound was prepared from ethyl 4,5-dihydro-4-oxo-5-phenylpyrano[3,2-b]indole-2-carboxylate. Several recrystallizations of the final product from acetone or aqueous DMF yielded white needles of mp 263°–265° C.

Preparation 4

4,5-Dihydro-5-methyl-4-oxopyrano[3,2-b]indole-2-carbonitrile

A mixture of 10.5 g (43.3 mmole) 4,5-dihydro-5-methyl-4-oxopyrano[3,2-b]indole-2-carboxamide, 12.6 g (66.2 mmole) p-toluenesulfonyl chloride, and 10.3 g (10.5 ml, 130 mmole) of pyridine in 55 ml DMF was heated under nitrogen on a steam bath for 4 hr. The cooled mixture was added to 500 g ice/water, stirred for 20 min, and the pink solid was filtered and washed with cold water. Two recrystallizations from ethanol yielded light pink needles of mp 190°–192° C.

Preparation 5

4,5-Dihydro-5-ethyl-4-oxopyrano[3,2-b]indole-2-carbonitrile

In a manner analogous to that of Preparation 4, the title compound was prepared from 4,5-dihydro-5-ethyl-4-oxopyrano[3,2-b]indole-2-carboxamide. Several recrystallizations from ethanol yielded yellow needles of mp 183.5°–185° C.

Preparation 6

4,5-Dihydro-4-oxo-5-phenylpyrano[3,2-b]indole-2-carbonitrile

In a manner analogous to that of Preparation 4, the title compound was prepared from 4,5-dihydro-4-oxo-5-phenylpyrano[3,2-b]indole-2-carboxamide. Recrystallization from ethanol or acetonitrile yielded pink needles of mp 191.5°–193° C.

Preparation 7

4,5-Dihydro-5-methyl-8-nitro-4-oxopyrano-[3,2-b]indole-2-carboxylic acid 8.2 g (33.7 mmole) of 4,5-dihydro-5-methyl-4-oxopyrano[3,2-b]indole-2-carboxylic acid was added over a few minutes to 80 ml of concentrated sulfuric acid cooled in ice. When solution was complete, 3.5 g (34.6 mmole) of potassium nitrate was added in portions over 30 min. The mixture was stirred in ice for a total of 5 hours, then poured over 750 g ice/water. The crude product was filtered, stirred briefly in 200 ml 50% aqueous ethanol, and re-filtered. Two recrystallizations from DMF-water yielded the acid product as a hemi-hydrate, fine yellow needles of mp 295° C. dec.

Preparation 8

4,5-Dihydro-5-methyl-6,8-dinitro-4-oxopyrano[3,2-b]indole-2-carboxylic acid 6.0 g (24.7 mmole) of 4,5-dihydro-5-methyl-4-oxopyrano[3,2-b]indole-2-carboxylic acid was added over a few minutes to 22 ml of concentrated sulfuric acid cooled in ice. Concentrated nitric acid (3.0 ml, 48 mmole) was then added in one portion, and the mixture was stirred and heated on the steam bath for 30 min. The cooled mixture was added to 300 g ice/water, and the crude product was filtered and washed with cold water. Two recrystallizations from DMF-water yielded yellow needles of mp 265° C. dec.

We claim:

1. A compound having the structural formula

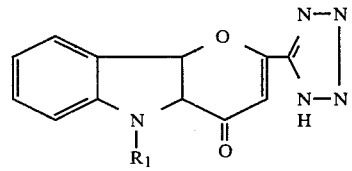

wherein $R_1$ is alkyl of from 1 to 6 carbon atoms or phenyl, and the pharmaceutically acceptable salts thereof.

2. The compound as defined in claim 1 wherein R is hydrogen, $R_1$ is methyl,

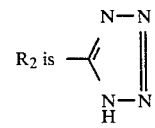

and the pharmaceutically acceptable salts thereof.

3. The compound as defined in claim 1 wherein R is hydrogen, $R_1$ is ethyl, $R_2$ is

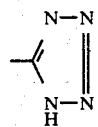

and the pharmaceutically acceptable salts thereof.

4. The compound as defined in claim 1 wherein R is hydrogen, $R_1$ is phenyl, $R_2$ is 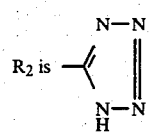

and the pharmaceutically acceptable salts thereof.

5. A compound having the structural formula

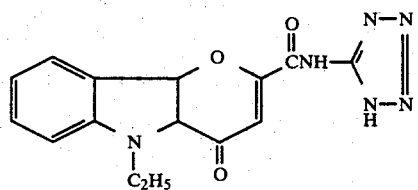

and the pharmaceutically acceptable salts thereof.

6. A compound having the structural formula

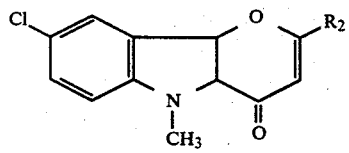

wherein $R_2$ is 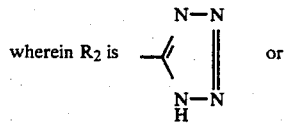 or

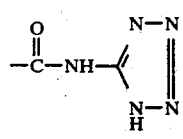

and the pharmaceutically acceptable salts thereof.

7. The compound as defined in claim 6 wherein R is 8-chloro, $R_1$ is methyl, $R_2$ is 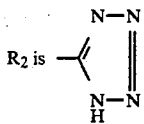

and the pharmaceutically acceptable salts thereof.

8. The compound as defined in claim 6 wherein R is 8-chloro, $R_1$ is methyl, $R_2$ is 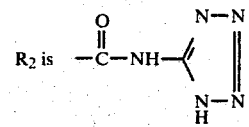

and the pharmaceutically acceptable salts thereof.

9. A compound having the structural formula

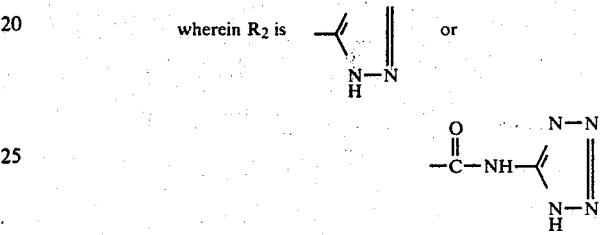

wherein $R_2$ is 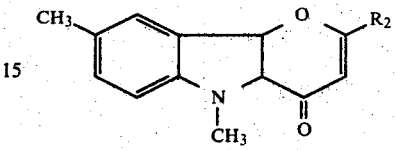 or

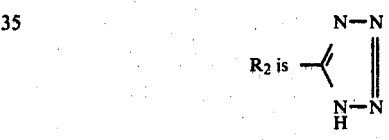

and the pharmaceutically acceptable salts thereof.

10. The compound as defined in claim 9 wherein R is 8-methyl, $R_1$ is methyl, $R_2$ is 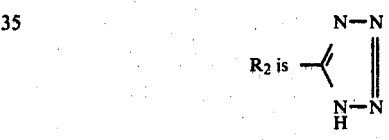

and the pharmaceutically acceptable salts thereof.

11. The compound as defined in claim 9 wherein R is 8-methyl, $R_1$ is methyl, $R_2$ is 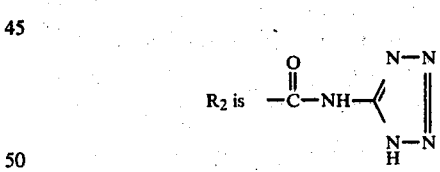

and the pharmaceutically acceptable salts thereof.

12. A compound having the structural formula

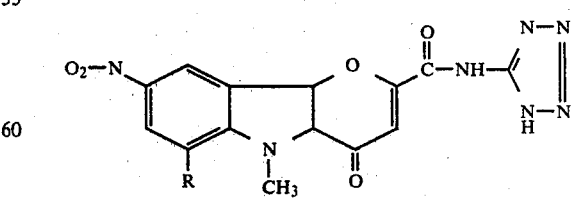

wherein R is hydrogen or nitro, and the pharmaceutically acceptable salts thereof.

13. The compound as defined in claim 12 wherein R is 8-nitro, $R_1$ is methyl, $R_2$ is

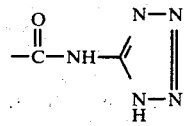

and the pharmaceutically acceptable salts thereof.

14. The compound of claim 12 wherein R is 6,8-dinitro, R₁ is methyl, R₂ is

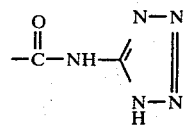

and the pharmaceutically acceptable salts thereof.

15. A pharmaceutical composition for preventing the allergic response in a mammal comprising an antiallergic effective amount of a compound as defined in claims 1, 5, 6, 9 or 12, and the pharmaceutically acceptable salts thereof.

16. A method of preventing the allergic response in a mammal which comprises administering to said mammal an antiallergic effective amount of a composition as defined in claim 15.

* * * * *